United States Patent [19]

Knoepfler

[11] Patent Number: 5,273,534
[45] Date of Patent: Dec. 28, 1993

[54] LAPAROSCOPIC T-TUBE, DRAIN AND SECURING INSTRUMENT AND METHOD THEREFOR

[76] Inventor: Dennis J. Knoepfler, 1383 Whitaker La., Amelia, Ohio 45102

[21] Appl. No.: 842,433

[22] Filed: Feb. 27, 1992

[51] Int. Cl.⁵ ............................................. A61M 29/00
[52] U.S. Cl. ..................................... 604/96; 604/284; 606/192
[58] Field of Search .................... 604/40–44, 604/96, 264, 280–284, 101; 606/191, 192, 194, 195

[56] References Cited

U.S. PATENT DOCUMENTS

| | | |
|---|---|---|
| 2,587,910 | 3/1952 | Shulman . |
| 2,624,341 | 1/1953 | Wallace ............................ 604/284 |
| 2,854,982 | 10/1958 | Pagano . |
| 3,835,863 | 9/1974 | Goldberg et al. . |
| 4,062,360 | 12/1977 | Bentley . |
| 4,072,153 | 2/1978 | Swartz ............................... 604/284 |
| 4,230,119 | 10/1980 | Blum . |
| 4,263,917 | 4/1981 | Moss . |
| 4,309,994 | 1/1982 | Grunwald ........................ 604/284 |
| 4,449,522 | 5/1984 | Baum ................................ 604/284 |
| 4,547,187 | 10/1985 | Kelly ................................ 604/284 |
| 4,704,102 | 11/1987 | Guthery . |
| 4,734,094 | 3/1988 | Jacob et al. ..................... 604/284 |
| 4,800,901 | 1/1989 | Rosenberg . |
| 4,804,359 | 2/1989 | Grumwald et al. ............. 604/284 |
| 4,840,172 | 6/1989 | Augustine et al. . |
| 5,007,898 | 4/1991 | Rosenbluth et al. . |
| 5,041,101 | 8/1991 | Seder et al. . |
| 5,108,364 | 4/1992 | Takezawa et al. . |
| 5,116,327 | 5/1992 | Seder et al. ..................... 604/284 |

OTHER PUBLICATIONS

Ideas for Medicine, inc., Reddick Cystic Duct, Hutson Common Duct, Cholangiography Catheters.

*Primary Examiner*—C. Fred Rosenbaum
*Assistant Examiner*—Manuel Mendez
*Attorney, Agent, or Firm*—Wood, Herron & Evans

[57] ABSTRACT

A combination laparoscopic T-tube, drain and balloon instrument comprises T-tube means, drain means, and balloon means and is insertable into a common bile duct and operable to evacuate fluids therefrom. The drain means is adjacent the T-tube means and is operable to evacuate fluids from the abdominal cavity and the balloon means is adjacent the T-tube means and drain means and is operable to fixate the T-tube within the common bile duct. To insert the instrument through a cannula and into a common bile duct, a V-tip stylet is provided which is a slender rigid rod with a V-tip on a distal end of the rod. A method is provided whereby the V-tip stylet is utilized to introduce the instrument through a cannula and into a common bile duct. In another embodiment, the invention comprises a T-tube, a drain adjacent the T-tube, and a flexible resilient member connected to the ends of the T-tube for configuring the T-tube generally straight for insertion into a bile duct, and for configuring the T-tube into a generally T configuration within the bile duct. The T-tube and drain are joined so as to function as an integral instrument.

14 Claims, 5 Drawing Sheets

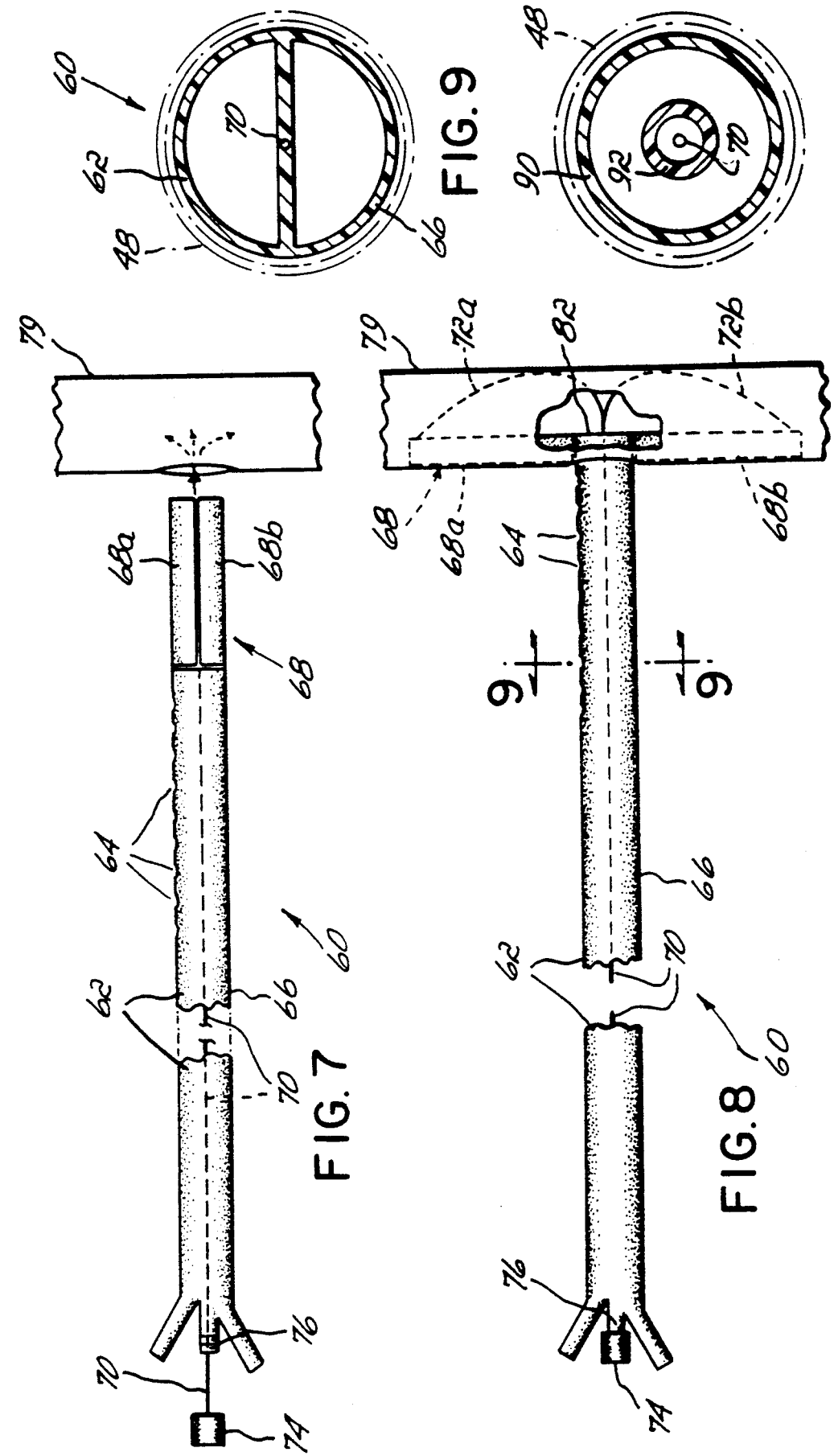

LAPAROSCOPIC T-TUBE, DRAIN AND SECURING INSTRUMENT AND METHOD THEREFOR

FIELD OF THE INVENTION

This invention relates to surgical instruments, and more particularly to a T-tube, stem drain and balloon or securing device combined into a single instrument for use during a laparoscopy.

BACKGROUND OF THE INVENTION

A common laparoscopic procedure performed by many general surgeons is the removal of the gall bladder. To perform this procedure laparoscopically, a number of cannulas, which are slender hollow tubes, are inserted into a patient's abdomen in the appropriate locations. Various medical instruments are then inserted through the cannulas into the abdomen to the operative site, and the gall bladder is removed. During this procedure an operative cholangiogram may be performed and if stones are found in the common bile duct a common bile duct exploration can be performed laparoscopically. After this procedure, it is common to insert a catheter into the common bile duct in order that bile may be drained and collected from the duct. However, present methods of draining the common bile duct with a catheter have proved disadvantageous in many respects.

Specifically, it is common to use what is known as a T-tube catheter to drain the common bile duct. Essentially, this T-tube catheter comprises a length of flexible tubing having a flexible T portion on one end. The T portion must be manipulated such that both ends of the T portion are inserted into the opening in the bile duct. This normally requires that the T portion be straightened for insertion. Once inside the duct, the T portion of the T-tube is released and springs back to resume its T shape. Normally the duct must be sutured in order to fixate the T portion of the T-tube within the bile duct.

It will be appreciated, however, that such a catheter having a T portion on an end thereof is not conducive for insertion through a slender cannula into a patient's abdomen for installation in the common bile duct. Specifically, the T portion thereof prevents, or at best renders difficult, such insertion through the cannula.

Another drawback of conventional T-tubes is the need to, as previously mentioned, suture these T-tubes in place. This procedure is extremely time and labor intensive, and somewhat difficult and tedious to perform laparoscopically.

Even with the T-tube in place in the common bile duct, such that bile can be drained therefrom, it is inevitable that some bile will escape from the bile duct at the location where the T-tube enters the bile duct. This bile and excess fluid therefore escapes from the bile duct into the patient's abdomen. This is generally undesirable and frequently requires a second drain.

SUMMARY OF THE INVENTION

It is therefore an object of the present invention to provide a laparoscopic T-tube which is easily insertable through a cannula and into a common bile duct for use during a laparoscopy.

It is another object of the present invention to provide a T-tube which can be fixed within a common bile duct without having to suture it in place.

It is yet another object of the present invention to provide a medical instrument which drains bile and fluids from a patient's abdomen which have escaped from the common bile duct and have not been collected by the T-tube drain.

It is still a further object of the present invention to provide a combination surgical instrument insertable through a single cannula thereby avoiding multiple portal entries into a patient's abdomen.

In accordance with the stated objects, a combination laparoscopic T-tube, drain and balloon or securing device instrument is provided. The instrument comprises a T-tube means which is insertable into a common bile duct within a patient's abdominal cavity to evacuate fluids from the common bile duct, a drain means adjacent the T-tube to evacuate fluids from the abdominal cavity, and a balloon means adjacent the T-tube and drain which can fix the T-tube within the common bile duct.

The T-tube means comprises an elongated tube having a T portion on its distal end and a proximal end which can be attached to a bile bag to aid in evacuating and collecting fluids from the common bile duct.

The drain means comprises an elongated tube having a plurality of openings along its distal end and a proximal end which can be attached to a vacuum bulb to aid in evacuating and collecting the fluids from the abdominal cavity.

The balloon means comprises an elongated tube having an inflatable balloon on a distal end and a proximal end which can be attached to a syringe to inflate the balloon with saline for fixing the balloon and the T portion of the T-tube within the common bile duct.

The respective tubes of the T-tube, drain and balloon are connected along lengths thereof to provide one integral combination instrument easily manipulated and inserted through a cannula. The instrument is thereby fabricated so as to function as an integral, unitary instrument conducive for insertion through a cannula into a patient's abdomen, thereby requiring only a single portal entry.

A V-tip stylet is provided for inserting the instrument through a cannula and into the common bile duct. The stylet comprises a slender rigid rod with a V-tip on its distal end. The V-tip deflects the T portion of the T-tube into a substantially straight configuration for insertion through the cannula into the common bile duct.

According to another aspect of the present invention a method is provided whereby the V-tip stylet is utilized to introduce the combination instrument through a cannula and into a common bile duct.

In another embodiment of the invention, a combination laparoscopic T-tube, drain and securing device instrument comprises a T-tube, a drain adjacent the T-tube, and a flexible resilient member connected to the ends of the T-tube for configuring the T-tube generally straight for insertion into a bile duct, and for configuring the T-tube into a generally T configuration within the bile duct. As with the first embodiment, the T-tube and drain are joined so as to function as an integral instrument.

One advantage of the present invention is that a surgical instrument has been provided which provides for the use of a T-tube, which T-tube can be used during a laparoscopic procedure.

Another advantage of the present invention is that a T-tube instrument has been provided which does not require suturing in place to secure same within the bile duct.

Yet another advantage of the present invention is that a combination T-tube, drain and balloon or securing device instrument is provided wherein the instrument can be used during a laparoscopy and which instrument not only drains fluids from the bile duct but also from a patient's abdominal cavity.

Still another advantage of the present invention is that a V-tip stylet has been provided which facilitates easy insertion of a T-tube through a cannula and into the common bile duct.

A further advantage of the present invention is that a combination instrument has been provided which eliminates the need for multiple portal entries into a patient's abdomen, as the combination instrument may be inserted through a single cannula.

These and other objects and advantages of the present invention will become more readily apparent during the following detailed description taken in conjunction with the drawings herein, in which:

BRIEF DESCRIPTION OF THE DRAWINGS

FIG. 7 is a plan view of an alternative embodiment of the present invention readied for insertion into a common bile duct;

FIG. 8 is a view similar to FIG. 7 illustrating the invention inserted into the common bile duct;

FIG. 9 is a view taken along lines 9—9 of FIG. 8, illustrating the cross-section of this embodiment of the invention;

FIG. 11 is a view similar to FIG. 9 illustrating an alternative cross-section of the embodiment of FIGS. 7-8.

DESCRIPTION OF THE PREFERRED EMBODIMENTS

Figure 1:
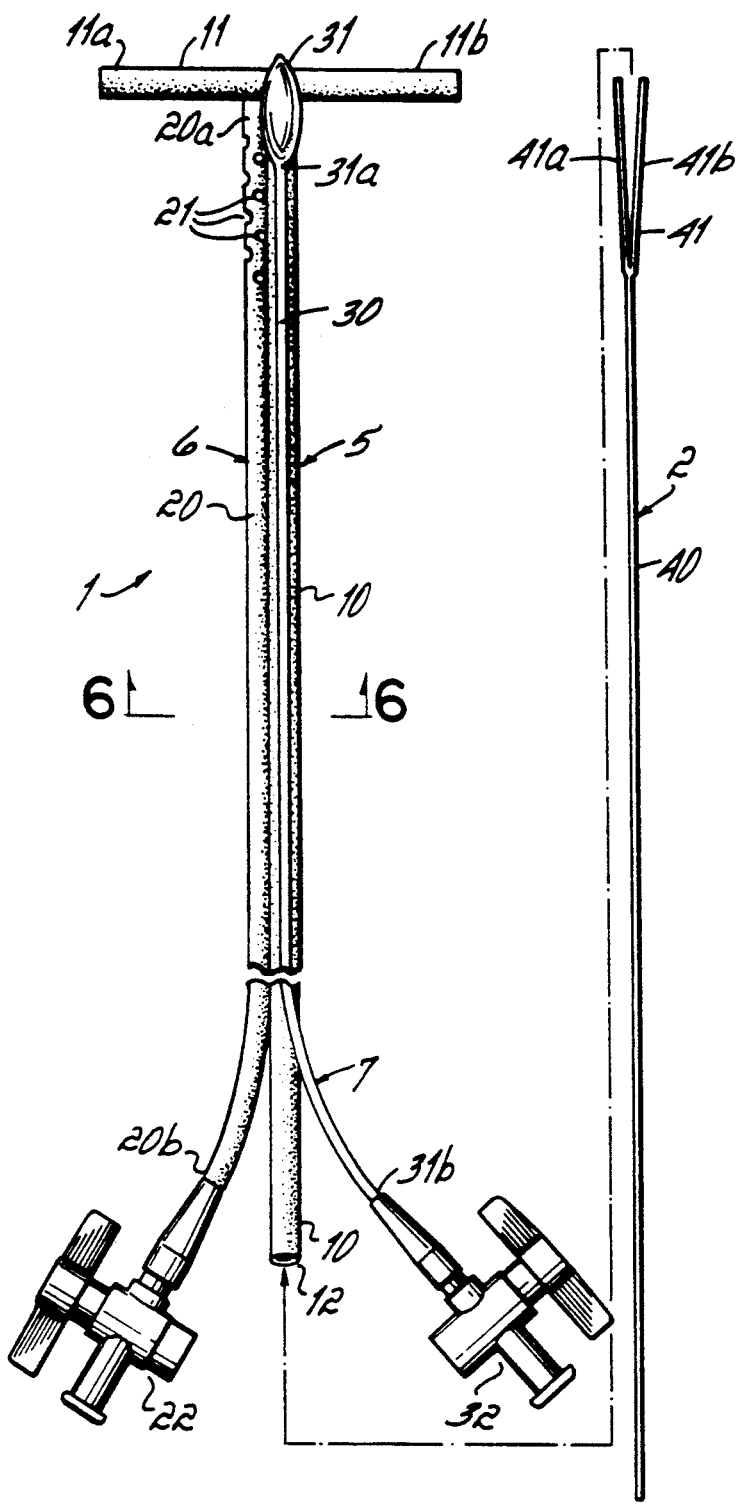
FIG. 1 is a plan view of the combination laparoscopic T-tube, drain and balloon instrument of the present invention and the V-tip stylet used to insert the combination instrument through a cannula into a common bile duct.

With reference first to FIG. 1, there is illustrated a combination laparoscopic T-tube, drain and balloon instrument 1, and V-tip stylet 2, of the present invention.

The instrument 1 comprises, generally, in combination a T-tube instrument 5, a drain instrument 6, and a balloon instrument 7. The T-tube 5, drain 6 and balloon 7 may be fabricated of latex or silicone rubber, or polyethylene, and may be extruded integrally, or may be fabricated separately and joined along their respective lengths, as by heat welding.

Figure 5:
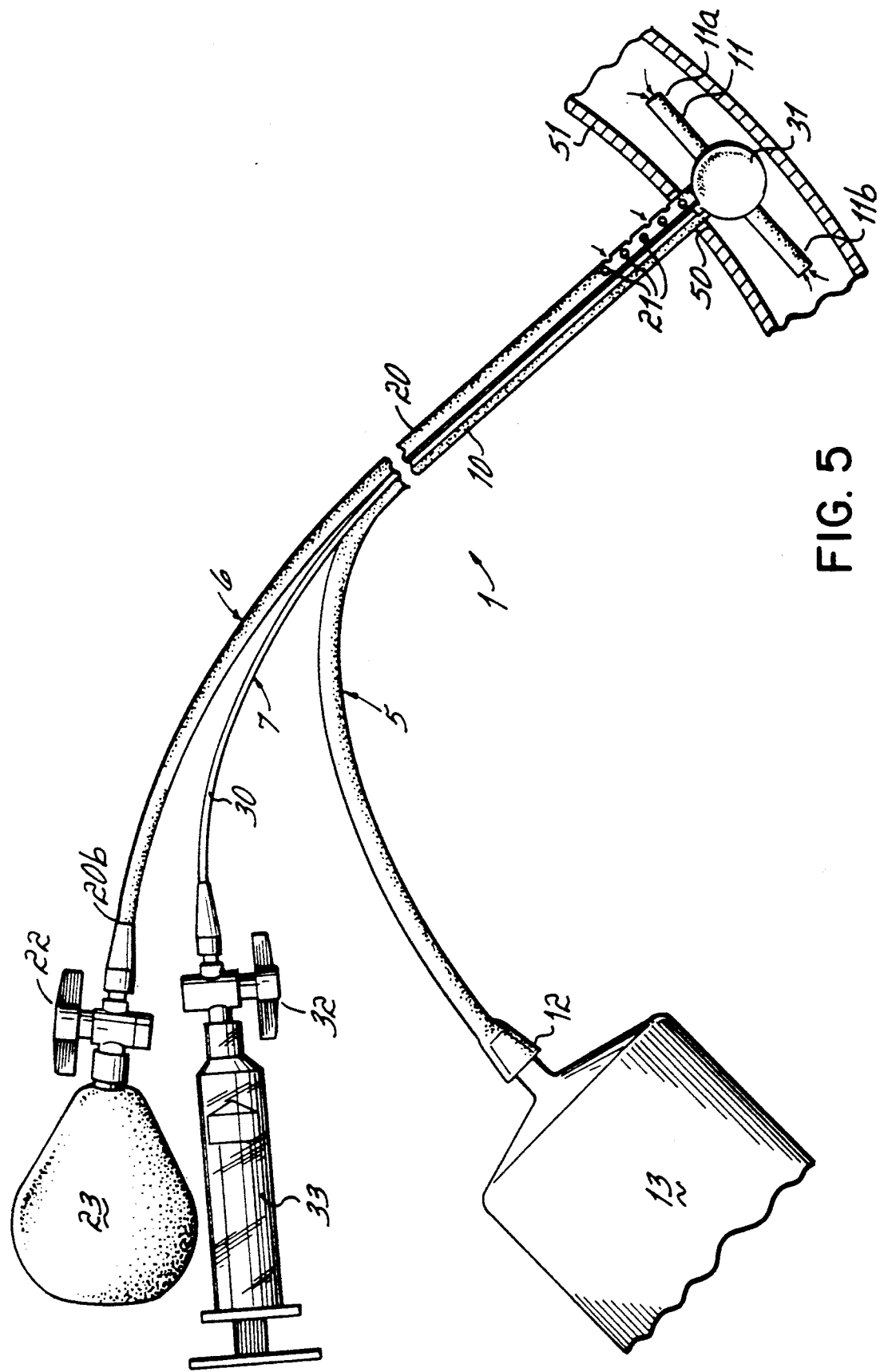
FIG. 5 illustrates use of the invention with a bile bag, a vacuum bulb and a syringe for collecting fluids and inflating the balloon.

The T-tube 5 comprises an elongated hollow tube 10 and a T portion 11 which has ends 11a and 11b on a distal end of the tube 10. Conventional means may be provided on a proximal end 12 for attaching a bile bag 13 (FIG. 5).

Drain instrument 6 includes an elongated hollow tube 20 having a plurality of openings 21 along a distal end 20a. A conventional valve 22 is provided on a proximal end 20b of the tube 20 for attaching a vacuum bulb 23 (FIG. 5).

The balloon instrument 7 comprises an elongated hollow tube 30 having an inflatable balloon 31 on a distal end 31a thereof and a conventional valve 32 on a proximal end 31b for attaching a syringe 33 (FIG. 5) for inflating the balloon 31 with saline.

Figure 6:
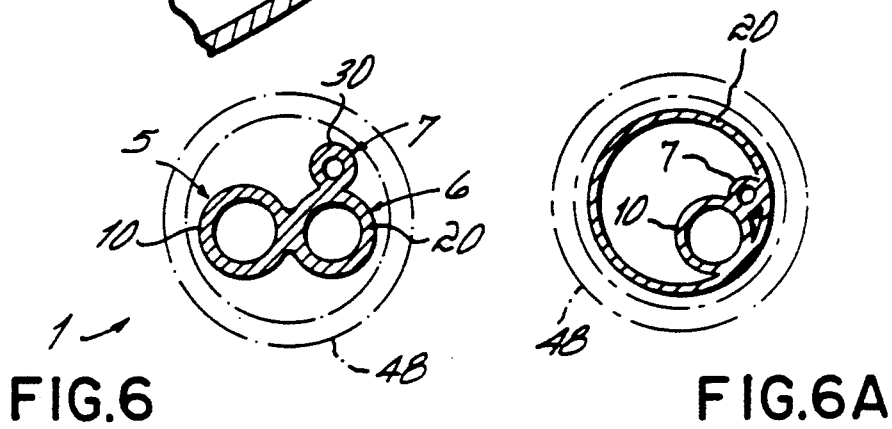
FIG. 6 is a view taken alone lines 6—6 of FIG. 1, illustrating the cross-section of the instrument of the invention.
Figure 6A:
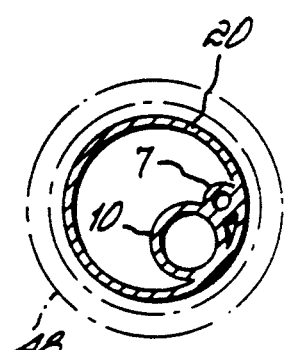
FIG. 6A is a view similar to FIG. 6 illustrating an alternative cross-section of the instrument.

With reference to FIG. 6, a cross-section of the instrument 1 is shown within a cannula 48. Tube 10 of the T-tube 5 is illustrated as being integrally connected to tube 20 of drain instrument 6, with tube 30 of balloon instrument 7 being connected to tube 20 of drain instrument 6. The respective tubes of the T-tube 5, drain 6 and balloon 7 could of course be integrally connected in many other ways, and the invention is not to be limited to the manner of connection shown in FIG. 6, as such is merely for illustrative purposes only. For example, an alternative construction is shown in FIG. 6A wherein tubes 7 and 10 are connected and are then themselves connected to the interior of tube 20, thereby rendering tubes 10 and 7 totally contained within the tube 20.

Figure 2:
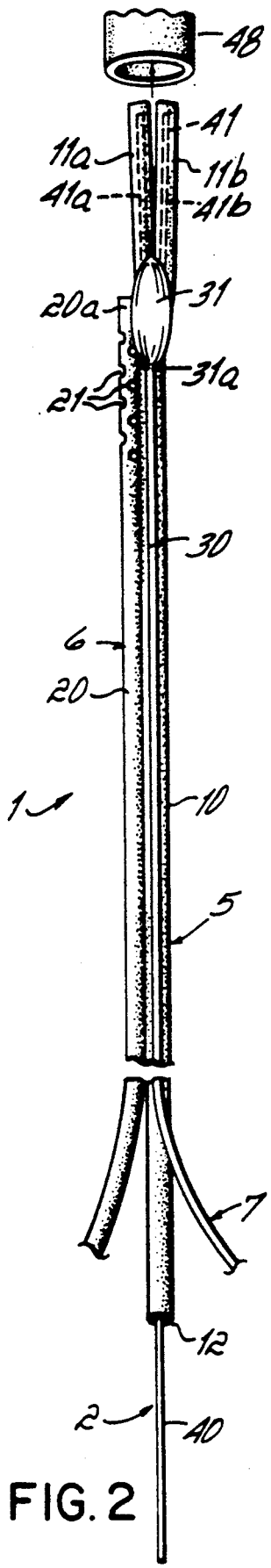
FIG. 2 illustrates the instrument of FIG. 1 with the V-tip stylet inserted into the T-tube such that the instrument may be inserted through a cannula and into a common bile duct.

The V-tip stylet 2, which aids in inserting the instrument 1 through a cannula and into a common bile duct, is fabricated of plastic or stainless steel and comprises a slender rigid rod 40 and a V-tip or prong 41 having ends 41a and 41b on a distal end of the rod 40. With reference to FIG. 2, it will be seen that insertion of the V-tip or prong 41 into the proximal end 12 of the tube 10 of the T-tube 5 enables the V-tip stylet 2 to be advanced towards the distal end of the tube 10 and hence the T portion 11. Continued advancement of the V-tip stylet 2 into the T-tube 5 causes each tip or prong 41a and 41b of the V-tip 41 to go into one of the tubes 11a and 11b of the T portion 11 causing them to assume a substantially straight configuration as illustrated in FIG. 2. This permits the entire instrument 1 to be inserted through a cannula 48 in a patient's abdomen and into a common bile duct, as will be subsequently described.

Figure 3:
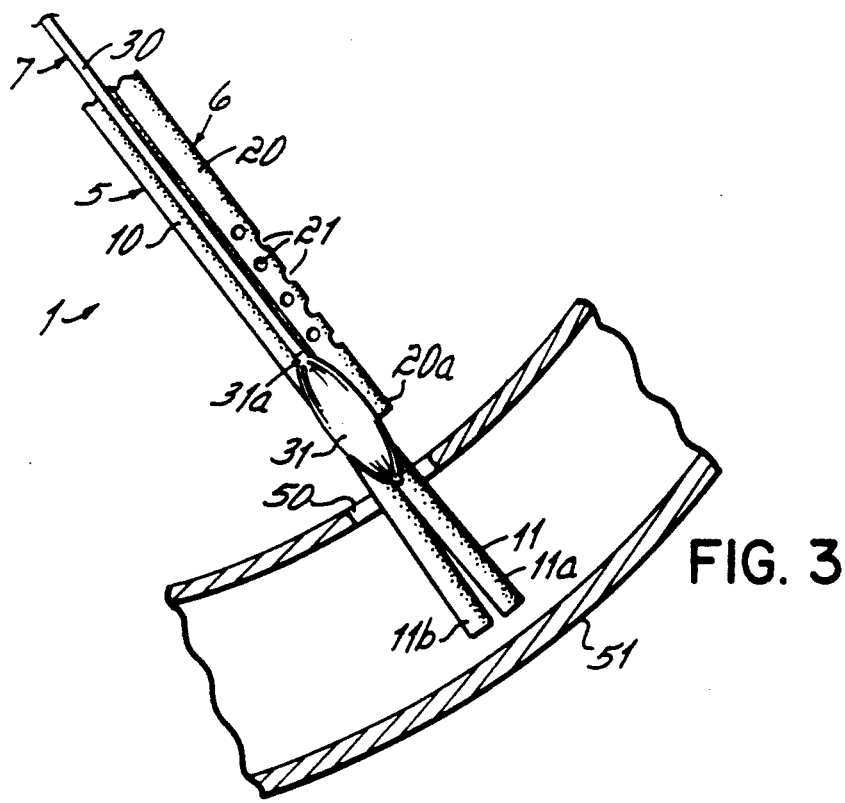
FIG. 3 is an enlarged view of the T portion of the T-tube of the present invention being inserted into a common bile duct with the use of the V-tip stylet.
Figure 4:
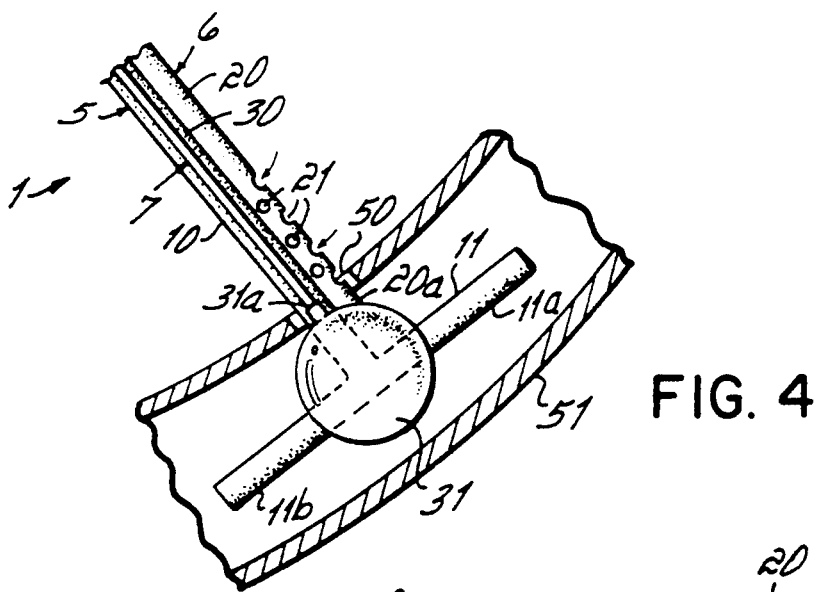
FIG. 4 is a view similar to FIG. 3 but illustrating the T-tube fully inserted within the common bile duct, the T portion having resumed its original configuration, and the balloon being inflated so as to fixate the T portion within the common bile duct.

With reference to FIG. 3, insertion of the instrument 1 into an opening 50 in a common bile duct 51 is illustrated. After the T portion 11 of the T-tube 5 has been inserted completely into the duct 51, the V-tip stylet 2 is withdrawn. The T portion 11 of the T-tube 5 then resiliently springs back resuming its original undeflected state within the duct 51. The balloon 31 is then inflated with saline from the syringe 33, such that the T portion 11 becomes fixed within the duct 51 and cannot be removed through opening 50. Of course it is readily apparent that the T-tube 5 will drain bile and fluids from within the bile duct 51, while the drain instrument 6 will drain fluids from the abdominal cavity in the vicinity of bile duct 51 generally through openings 21.

Figures 10, 10A:
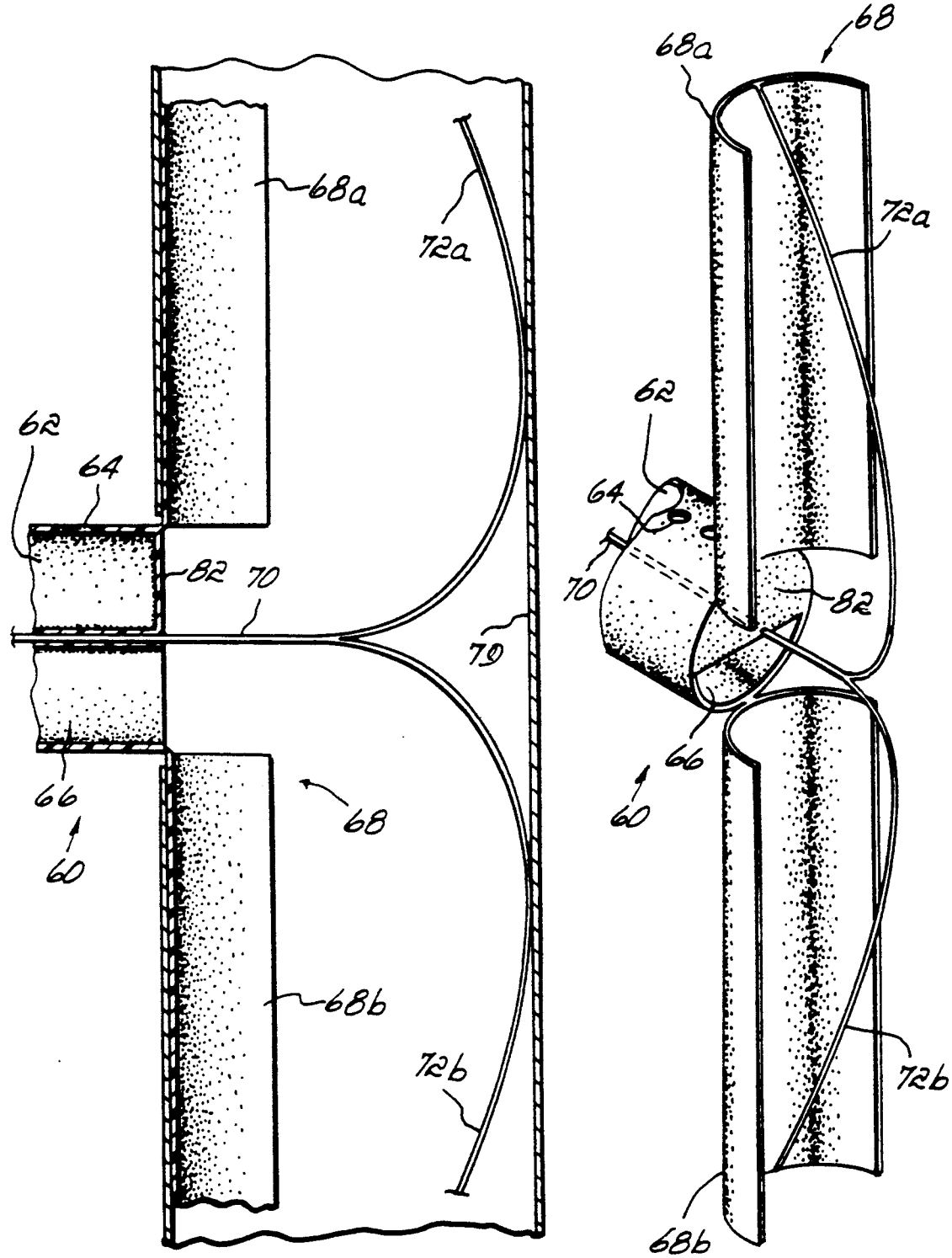
FIG. 10 is an enlarged view of the T-portion of the embodiment of FIGS. 7-9.
FIG. 10A is a view similar to FIG. 10 but in perspective.

With reference now to FIGS. 7-10A, there is illustrated an alternative form of the present invention 60 which alleviates the need for a V-tipped stylet to insert the instrument through a cannula and into a common bile duct. The instrument 60 includes a stem drain 62 having a plurality of openings 64 in a distal end thereof, and a T-tube 66 adjacent to stem drain 62. As can be seen from FIG. 9, stem drain 62 forms the upper hemisphere of the instrument, while the T-tube drain 66 forms the lower hemisphere of the instrument. The T-tube 66 includes a T portion 68 including ends 68a and 68b both of which are themselves generally hemispherically shaped (FIG. 10A).

Each of the ends 68a and 68b is connected to a central wire 70 via flexible yet resilient leaders 72a and 72b, respectively. The leaders 72a, 72b in their undeflected state maintain the ends 68a, 68b of the T portion 68 of the T-tube 66 in a generally linear configuration (FIG. 7) for insertion into common bile duct 79. By advancing a threaded knob 74, to which the proximal end of central wire 70 is attached, forwardly and securing same to a threaded portion 76 of the instrument, the leaders 72a, 72b force the ends 68a and 68b of the T portion 68 of the T-tube outwardly generally perpendicular to the tube 66 within the duct 79.

The leaders 72a, 72b may be fabricated from any resilient and generally corrosion resistant material, such as plastic, thin stainless steel, or the like. Undeflected the leaders 72a, 72b maintain the T portion 68 generally straight, and upon being advanced forwardly force the T portion 68 into a generally T configuration.

As can be seen from FIG. 8, the leaders 72a and 72b abut against the forwardmost inner surface 78 of the common bile duct 79 thereby forcing the ends 68a and 68b against the opposite inner surface 80 of the common bile duct 79, thereby eliminating the need to suture the instrument in place.

With reference to FIG. 10, it will be seen that the T-tube 66 is operable to drain bile from the common bile duct through the lower hemisphere of the instrument 60, the upper hemisphere of the instrument (drain 62) being closed at its proximal end by a hemispherical wall 82.

An alternative cross-sectional form of this embodiment of the invention is illustrated in FIG. 11. In cross-section, the instrument includes an outermost drain tube 90 within which is located the T-tube 92. In all other respects, this embodiment is the same as that illustrated in FIGS. 7-10.

From the above detailed description it is readily apparent that the instrument of the present invention has numerous features and advantages. No suturing is required to fixate the T-tube within a bile duct. Only a single portal entry is required in a patient's abdomen to introduce the instrument. And, insertion of the T-tube into a common bile duct has been facilitated.

Those skilled in the art will readily recognize adaptations and modifications which can be made to the present invention and which will result in an improved combination laparoscopic T-tube, drain and balloon or securing device instrument, yet all of which will fall within the spirit and scope of the present invention as defined in the appended claims. Accordingly, I intend to be limited only by the claims.

What is claimed is:

1. A combination laparoscopic T-tube, drain and balloon instrument comprising:

resilient T-tube means having a T-portion on the distal end and having undeflected and deflected states and being deformable to its deflected state so as to be insertable into and through a cannula and into a common bile duct within a patient's abdominal cavity and being operable to evacuate fluids from said common bile duct, said T-portion of said T-tube means being operable to resume its undeflected state upon insertion into said bile duct, drain means adjacent said T-Tube means having an opening on the distal end and being operable to evacuate fluids from said abdominal cavity in a general vicinity of said bile duct, and balloon means adjacent said T-tube means and drain means and being operable to fixate said T-tube means within said common bile duct;

said T-tube means, drain means and balloon means being joined so as to function as an integral instrument.

2. The instrument of claim 1 wherein said T-tube means comprises an elongated tube, said T portion being on a distal end thereof and means on a proximal end thereof for attaching a bile bag thereto to aid in evacuating and collecting said fluids from said common bile duct.

3. The instrument of claim 1 wherein said drain means comprises an elongated tube having a plurality of openings along a distal end thereof and means on a proximal end thereof for attaching a vacuum bulb thereto to aid in evacuating and collecting said fluids from said abdominal cavity.

4. The instrument of claim 1 wherein said balloon means comprises an elongated tube having an inflatable balloon on a distal end thereof and means on a proximal end thereof for connecting a syringe thereto to inflate said balloon with saline for fixating said balloon and said T-tube means within said common bile duct.

5. The instrument of claim 1 wherein:

said T-tube means comprises an elongated tube having a T portion on a distal end thereof and means on a proximal end thereof for attaching a bile bag thereto to aid in evacuating and collecting said fluids from said common bile duct;

said drain means comprises an elongated tube having a plurality of openings along a distal end thereof and means on a proximal end thereof for attaching a vacuum bulb thereto to aid in evacuating and collecting said fluids from said abdominal cavity;

said balloon means comprises an elongated tube having an inflatable balloon on a distal end thereof and means on a proximal end thereof for connecting a syringe thereto to inflate said balloon with saline for fixating said balloon and said T portion of said T-tube means within said common bile duct; and said T-tube means, drain means and balloon means being connected together along respective lengths of respective tubes thereof to form an integral, unitary instrument, said T-tube means T portion and said balloon means balloon being positioned generally adjacent said distal end of said drain means.

6. A combination laparoscopic T-tube, drain and balloon instrument comprising:

T-tube means being insertable into a common bile duct within a patient's abdominal cavity and being operable to evacuate fluids from said common bile duct, drain means adjacent said T-Tube means and being operable to evacuate fluids from said abdominal cavity in a general vicinity of said bile duct, and balloon means adjacent said T-tube means and drain means and being operable to fixate said T-tube means within said common bile duct;

said T-tube means, drain means and balloon means being joined so as to function as an integral instrument;

each of said T-Tube means, drain means and balloon means including a respective elongated tube, said elongated tubes of said T-tube means and balloon means being contained within said elongated tube of said drain means, said elongated tube of said drain means having a plurality of openings along a distal end thereof, said elongated tube of said T-tube means having a T portion on a distal end thereof extending out of said distal end of said drain means elongated tube and said elongated tube of said balloon means having an inflatable balloon on a distal end thereof extending out of said distal end of said drain means elongated tube.

7. A combination laparoscopic T-tube, drain and balloon instrument comprising:

T-tube means being insertable into a common bile duct within a patient's abdominal cavity and being operable to evacuate fluids form said common bile duct, drain means adjacent said T-Tube means and being operable to evacuate fluids from said abdominal cavity in a general vicinity of said bile duct, and balloon means adjacent said T-tube means and drain means and being operable to fixate said T-tube means within said common bile duct;

said T-tube means, drain means and balloon means being joined so as to function as an integral instrument;

said T-tube means comprising an elongated tube having a T portion on a distal end thereof and means on a proximal end thereof for attaching a bile bag thereto to aid in evacuating and collecting said fluids from said common bile duct;

said drain means comprising an elongated tube having a plurality of openings along a distal end thereof and means on a proximal end thereof for attaching a vacuum bulb thereto to aid in evacuating and collecting said fluids from said abdominal cavity;

said balloon means comprising an elongated tube having an inflatable balloon on a distal end thereof and means on a proximal end thereof for connecting a syringe thereto to inflate said balloon with saline for fixating said balloon and said T portion of said T-tube means within said common bile duct;

said T-tube means, drain means and balloon means being connected together along respective lengths of respective tubes thereof to form an integral, unitary instrument;

said elongated tubes of said T-tube means and balloon means being contained within said elongated tube of said drain means, said T-tube means T portion and said balloon means inflatable balloon extending out of said distal end of said drain means elongated tube.

8. A V-tip stylet for insertion of a T-tube through a cannula and into a common bile duct comprising:

a slender rigid rod, and a rigid V-tip on a distal end of said rod;

said V-tip stylet being operable to deflect a T portion of said T-tube into a substantially straight configuration wherein said T portion may be inserted through a cannula and into a common bile duct, whereupon said V-tip stylet may be withdrawn allowing said T-tube to resume its undeflected shape within said bile duct.

9. A method of installing a combination laparoscopic T-tube, drain and balloon instrument through a cannula and into a common bile duct of a patient comprising the steps of:

inserting a V-tip stylet into a T-tube portion of said instrument and deflecting a T portion thereof into a substantially straight configuration;

inserting said combination instrument through said cannula and into said patient's abdomen;

inserting said straightened T portion of said T-tube portion and a balloon portion of said instrument into said bile duct;

withdrawing said V-tip stylet from said T-tube portion;

inflating said balloon portion of said instrument thereby fixating said T portion within said bile duct whereupon said T-tube portion is operable to drain bile and fluids for said bile duct; and whereupon a drain portion of said instrument is operable to drain bile and fluids from said patient's abdomen in a vicinity of said bile duct.

10. A combination laparoscopic T-tube, drain and securing device instrument comprising:

resilient T-tube means having a T-portion on the distal end and having undeflected and deflected states and being deformable to its deflected state so as to be insertable into and through a cannula and into a common bile duct within a patient's abdominal cavity and being operable to evacuate fluids from said common bile duct, said T-portion of said T-tube means being operable to resume its undeflected state upon insertion into said bile duct, drain means adjacent to said T-tube means having an opening on the distal end and being operable to evacuate fluids from said abdominal cavity in a general vicinity of said bile duct, and resilient means connected to said T-tube means and being operable to fixate said T-tube means within said common bile duct;

said T-tube means, drain means and resilient means being joined so as to function as an integral instrument.

11. The instrument of claim 10 wherein said T-tube means comprises an elongated tube, said T portion being on a distal end thereof and means on a proximal end thereof for attaching a bile duct thereto to aid in evacuating and collecting said fluids from said common bile duct.

12. The instrument of claim 10 wherein said drain means comprises an elongated tube having a plurality of openings along a distal end thereof and means on a proximal end thereof for attaching a vacuum bulb thereto to aid in evacuating and collecting said fluids from said abdominal cavity.

13. A combination laparoscopic T-tube, drain and securing device instrument comprising:

T-tube means being insertable into a common bile duct within a patient's abdominal cavity and being operable to evacuate fluids from said common bile duct, drain means adjacent to said T-tube means and being operable to evacuate fluids from said abdominal cavity in a general vicinity of said bile duct, and resilient means connected to said T-tube means and being operable to fixate said T-tube means within said common bile duct;

said T-tube means, drain means and resilient means being joined so as to function as an integral instrument;

said T-tube means comprising an elongated tube having a T portion on a distal end thereof and means on a proximal end thereof for attaching a bile bag thereto to aid in evacuating and collecting said fluids from said common bile duct;

14. A combination laparoscopic T-tube, drain and securing device instrument comprising:

T-tube means being insertable into a common bile duct within a patient's abdominal cavity and being operable to evacuate fluids from said common bile duct, drain means adjacent to said T-tube means and being operable to evacuate fluids form said abdominal cavity in a general vicinity of said bile duct, and resilient means connected to said T-tube means and being operable to fixate said T-tube means within said common bile duct;

said T-tube means, drain means and resilient means being joined so as to function as an integral instrument;

each of said T-tube means and drain means including a respective elongated tube, said T-tube elongated tube being contained within said drain means elongated tube, said T-tube means elongated tube having a T portion on a distal end, said T portion extending out of a distal end of said drain means elongated tube.

\* \* \* \* \*

UNITED STATES PATENT AND TRADEMARK OFFICE
CERTIFICATE OF CORRECTION

PATENT NO. : 5,273,534
DATED : December 28, 1993
INVENTOR(S) : Dennis J. Knoepfler It is certified that error appears in the above-identified patent and that said Letters Patent is hereby corrected as shown below:

Col. 7, line 29, "form" should be -- from --.

Col. 9, line 16, after duct; add a paragraph as follows:

-- said resilient means comprising a rod extending through said instrument, said rod having on a distal end thereof a pair of flexible resilient leaders, each of which is connected to an end of said T portion of said T-tube, whereby when said leaders are in an undeflected state said leaders configure said T portion of said T-tube generally straight, and when said central rod is advanced toward a distal end of said instrument said rod flexes said leaders forcing said T portion into a generally T configuration. --

Col. 10, line 4, "form" should be -- from --.

Signed and Sealed this

Fourth Day of October, 1994

*Attest:*

BRUCE LEHMAN

*Attesting Officer*  *Commissioner of Patents and Trademarks*